(12) United States Patent
Jacofsky et al.

(10) Patent No.: US 9,173,749 B2
(45) Date of Patent: Nov. 3, 2015

(54) SPINAL INTERBODY SPACER DEVICE AND METHODS OF USING SAME

(71) Applicant: The Center for Orthopedic Research and Education, Inc., Phoenix, AZ (US)

(72) Inventors: Marc C. Jacofsky, Phoenix, AZ (US); A. Joshua Appel, Paradise Valley, AZ (US)

(73) Assignee: The Center for Orthopedic Research and Education, Inc., Phoenix, AZ (US)

( * ) Notice: Subject to any disclaimer, the term of this patent is extended or adjusted under 35 U.S.C. 154(b) by 152 days.

(21) Appl. No.: 14/021,466

(22) Filed: Sep. 9, 2013

(65) Prior Publication Data

US 2014/0081404 A1 Mar. 20, 2014

Related U.S. Application Data

(62) Division of application No. 12/074,478, filed on Mar. 3, 2008, now Pat. No. 8,556,976.

(60) Provisional application No. 60/904,691, filed on Mar. 1, 2007.

(51) Int. Cl.
*A61F 2/44* (2006.01)
*A61B 17/70* (2006.01)
*A61B 17/58* (2006.01)
(Continued)

(52) U.S. Cl.
CPC ............ *A61F 2/4611* (2013.01); *A61F 2/447* (2013.01); *A61B 17/92* (2013.01); *A61F 2002/2835* (2013.01); *A61F 2002/3082* (2013.01); *A61F 2002/30594* (2013.01); *A61F 2002/4475* (2013.01); *A61F 2002/4619* (2013.01);
(Continued)

(58) Field of Classification Search
CPC ....... A61F 2/442; A61F 2/447; A61F 2/4455; A61F 2/4465
USPC ........................................................ 623/17.16
See application file for complete search history.

(56) References Cited

U.S. PATENT DOCUMENTS 5,176,678 A 1/1993 Tsou
5,658,336 A 8/1997 Pisharodi
(Continued)

OTHER PUBLICATIONS

Non-Final Office Action issued by the U.S. Patent & Trademark Office on Apr. 26, 2011 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (8 pages).

(Continued)

*Primary Examiner* — David Isabella
*Assistant Examiner* — Christine Nelson
(74) *Attorney, Agent, or Firm* — Ballard Spahr LLP (57) ABSTRACT

A method is provided for manipulating a spinal body spacer for use in spinal surgery on a patient. The method includes attaching a placement tool to the spinal body spacer and manipulating the placement tool so as to locate the spinal body spacer in a desired location. The placement tool can by removed by unscrewing the placement tool from a threaded receiving aperture of the spinal body spacer. The method also includes passing a tip of an extraction tool through the threaded receiving aperture of the spinal body spacer, the tip of the extraction tool having at least one tab. The tip of the extraction tool is rotated such that the at least one tab of the tip of the extraction tool passes through keyways of the spacer and extends into the interior space of the spinal body spacer.

17 Claims, 13 Drawing Sheets

(51) Int. Cl.
   *A61B 17/60* (2006.01)
   *A61F 2/00* (2006.01)
   *A61F 2/46* (2006.01)
   A61B 17/92 (2006.01)
   A61F 2/28 (2006.01)
   A61F 2/30 (2006.01)

(52) U.S. Cl.
   CPC . *A61F2002/4627* (2013.01); *A61F 2002/4629* (2013.01)

(56) References Cited

U.S. PATENT DOCUMENTS

| | | | |
|---|---|---|---|
| 5,683,463 | A | 11/1997 | Godefroy et al. |
| 5,888,224 | A | 3/1999 | Beckers et al. |
| 6,093,207 | A | 7/2000 | Pisharodi |
| 6,096,038 | A | 8/2000 | Michelson |
| RE37,005 | E | 12/2000 | Michelson et al. |
| 6,241,771 | B1 | 6/2001 | Gresser et al. |
| 6,245,108 | B1 | 6/2001 | Biscup |
| 6,264,657 | B1 | 7/2001 | Urbahns et al. |
| 6,503,279 | B1 | 1/2003 | Webb et al. |
| 6,652,533 | B2 | 11/2003 | O'Neil |
| 6,709,439 | B2 | 3/2004 | Rogers et al. |
| 6,767,366 | B2 | 7/2004 | Lee et al. |
| 6,814,738 | B2 | 11/2004 | Naughton et al. |
| 8,556,976 | B2 | 10/2013 | Jacofsky et al. |
| 2003/0028216 | A1 | 2/2003 | Hanson |
| 2003/0125739 | A1 | 7/2003 | Bagga et al. |
| 2003/0233145 | A1 | 12/2003 | Landry et al. |
| 2004/0117020 | A1* | 6/2004 | Frey et al. .................. 623/17.11 |
| 2004/0148028 | A1 | 7/2004 | Ferree et al. |
| 2008/0097435 | A1 | 4/2008 | DeRidder et al. |
| 2008/0288076 | A1 | 11/2008 | Soo et al. |

OTHER PUBLICATIONS

Amendment and Response to Non-Final Office Action filed on Jul. 25, 2011 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (13 pages).

Final Office Action issued by the U.S. Patent & Trademark Office on Oct. 20, 2011 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (9 pages).

Amendment and Response to Office Action filed on Dec. 20, 2011 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (11 pages).

Amendment and Response to Office Action filed on Feb. 21, 2012 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (11 pages).

Non-Final Office Action issued by the U.S. Patent & Trademark Office on Dec. 19, 2012 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (8 pages).

Amendment in Response to Non-Final Office Action filed on May 17, 2013 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (9 pages).

Supplemental Amendment in Response to Non-Final Office Action filed on May 17, 2013 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (10 pages).

Notice of Allowance and Fees Due issued by the U.S. Patent & Trademark Office on Dec. 19, 2012 for U.S. Appl. No. 12/074,478, filed Mar. 3, 2008 and granted as U.S. Pat. No. 8,556,976 on Oct. 15, 2013 (Inventor—Jacofsky // Applicant—The Center for Orthopedic Research) (13 pages).

* cited by examiner

SPINAL INTERBODY SPACER DEVICE AND METHODS OF USING SAME

CROSS REFERENCE TO RELATED APPLICATIONS

This application is a divisional of U.S. patent application Ser. No. 12/074,478, filed Mar. 3, 2008, which claims the benefit of the filing date of U.S. Provisional Patent Application No. 60/904,691, filed Mar. 1, 2007, which applications are incorporated herein by reference in their entirety.

FIELD

The present invention relates to medical devices. More particularly, the invention relates to interbody spacer devices and methods for their placement and extraction in spinal surgeries and therapies.

BACKGROUND

Interbody spacers are used as aids in various spinal surgeries. When a spinal disc has suffered disease or trauma, degeneration of one or more discs may result. Depending on the medical indications of the damaged spine, a surgical treatment may be called for. For example, spinal surgeries may call for the full or partial removal of a spinal disc. In other procedures, an implant or support may be used to stabilize elements of the spine in order to assist in the healing process. Various devices have been developed, some known as interbody spacers or spreaders, for use in one or more spinal surgeries. While these devices can be used in a variety of different surgeries and treatments, in several known surgical procedures it is necessary to physically implant an interbody spacer in a desired location relative to the spine. Later, depending on the treatment, the interbody spacer may or may not be removed from the patient.

However, the existing spacers suffer from a limited ability to extract and reposition the interbody spacer device. The limitation on repositioning is noted both during the initial placement and also later after the initial placement has occurred. This limitation is experienced in current devices, systems, and surgical procedures. This limitation introduces additional potential risks to the patient. With current systems and procedures, the need to remove or reposition an interbody spacer can present a significant risk to the patient's spinal cord, nerve roots, and dural sack. The fear of working with extraction tools in close proximity to the spinal cord may lead surgeons to perform more invasive techniques, such as a partial corpectomy, to retrieve the device without damaging the spinal cord. Similarly, a surgeon may settle for an imperfect placement due to the risk associated with introducing tools to reposition the device and a lack of options for repositioning. Hence, in order to overcome these limitations, it would be desired to provide an interbody spacer device that provides increased movement and flexibility after the initial positioning.

The device described herein allows a retrieval tool to be locked into the spacer block to ease removal or repositioning of the innerbody spacer. It can be configured in dimensions appropriate for transforaminal lumbar interbody fusion (TLIF), posterior lumbar interbody fusion (PLIF), and anterior lumbar interbody fusion (ALIF) procedures and is not limited to any one technique. The block is inserted using a newly developed threaded rod assembly using an insertion technique that is similar to techniques currently described by other manufacturers of TLIF devices. The device would preferably be manufactured from a material such as a PEEK or similar material. The block could be offered with multiple angle and height options to restore the proper lordosis and spacing at the level of fusion. The block contains voids with interconnections to allow bone graft or bone substitute to be packed inside and to promote tissue ingrowth within the spacer.

One innovation is the incorporation of an extraction tool that can be inserted and locked into the implant, allowing it to be pulled out with the aide of a slap hammer, or other surgical hammer, that allows for incremental movements and mitigates the risk of damaging the dural sac or spinal cord. The extraction tool consists of a blunt face "key" that can be passed into the spacer block and is then rotated 90 degrees to a positive stop so it cannot be withdrawn.

In most cases the need to remove the device will become apparent before significant tissue ingrowth and bone fusion have occurred. This may be due to incorrect initial positioning by the surgeon, infection shortly after surgery, or failure of a vertebral body. These issues usually become apparent within several weeks after initial surgery.

In the event that the implant has been in place for some time and significant scar tissue or trabecular bone ingrowth has occurred, an alternative tool, with a much sharper profile can be used to clear the inner void of the spacer and improve the chances of recovering the implant without resorting to more invasive methods.

SUMMARY

In one embodiment, and by way of example only, there is provided an instrument set for use in spinal surgery that includes: a spinal body spacer having a threaded opening and keyways connected to the threaded opening; a placement tool having a threaded tip for connecting with the threaded opening of the spacer; and an extraction tool with a tip configured to pass through the opening of the spacer, and the tool having tabs positioned on the tip such that the tabs pass through the keyways of the spacer. The spacer may have an outer face positioned around the opening and the placement tool may also have a contact face such that the contact face comes into contact with the outer face when the placement tool is fully connected with the spacer. The spinal body spacer may also include a superior surface and an inferior surface with a plurality of antimigration furrows positioned on each of the superior surface and the inferior surface. The tip of the extraction tool may be a substantially blunt tip, a substantially pointed tip, or even a tip with a hollow area. The spacer may have at least one block disposed on an interior surface such that the block contacts the tabs of the extraction tool thereby restricting rotation of the extraction tool relative to the spacer. The spacer may have a backing plate, and the backing plate may itself include projections disposed in the matrix of the spacer. The instrument set may further include a slap hammer having a keyed end configured to attach to the spacer. The spacer may be constructed with a body having a first wall and a second wall connected by a top face, a bottom face, and a lateral support.

In a further embodiment, still by way of example only, there is provided a method for manipulating a spinal interbody spacer for use in spinal surgery on a patient, in which the method includes the steps of: attaching a positioning tool to a spacer by screwing a threaded end of the positioning tool to threaded receiving aperture of the spacer; manipulating the positioning tool so as to locate the spacer in a desired location; and removing the positioning tool by unscrewing it from the threaded portion of the spacer. The method may further include the step of receiving positioning information from the spacer through radio opaque markets located in the spacer. Additionally the method may include the step of attaching a positioning tool and contacting a contact face positioned on the positioning tool with a reciprocal face positioned on the spacer so as to transfer force from the positioning tool to the spacer. Additionally, the method allows the step of securing the spacer to the surgical patient. Finally, the method may be used with further steps such as: sliding the tip of an extraction tool through an aperture in the spacer; rotating the tip of the extraction tool until tabs located on the extraction tool contact blocks positioned on the spacer; and pulling on the extraction tool so as to exert a force on the spacer.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention. Reference will now be made in detail to exemplary embodiments of the invention, examples of which are illustrated in the accompanying drawings. Wherever possible, the same reference numbers will be used throughout the drawings to refer to the same or like parts.

There is now described a set of elements which may be used in combination as an assembly or individually as an instrument set or a medical or surgical kit. Furthermore a method will be described for advantageously using the elements of the kit so as to overcome limitations previously described in the prior art for spinal spacers and implants.

Figure 1:
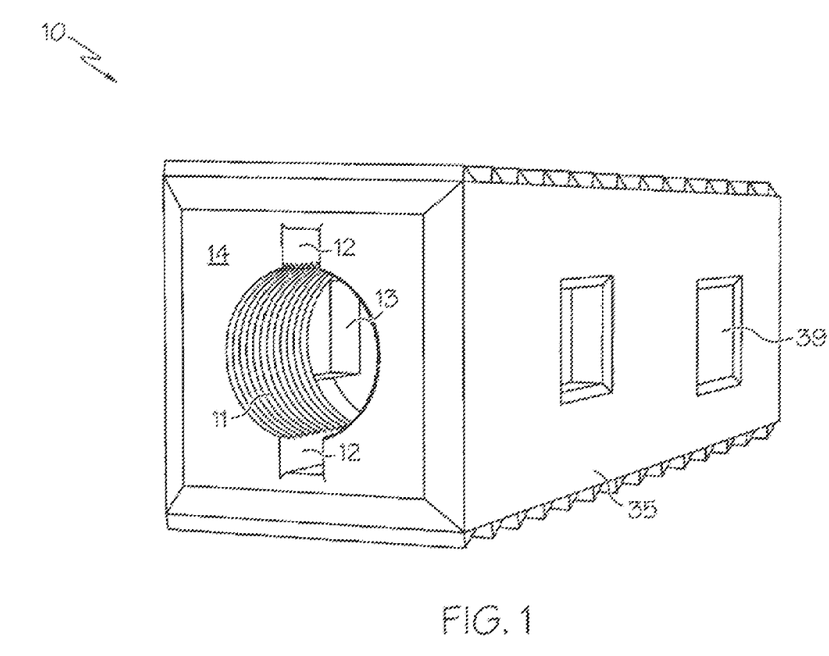
FIG. 1 is a perspective view of an interbody spacer device having a face with a keyway passage, according to an embodiment of the present invention.

Referring now to FIG. 1, the figure demonstrates an exemplary shape of a spinal interbody spacer 10. Spacer 10 includes threads 11 which allow a placement technique using a threaded rod assembly. The threaded rod (not shown) can engage with the threads 11 so as to allow a manipulation of the spacer 10 by the rod. The cutouts 12 shown in face 14 surrounding aperture 13 allow an extraction tool to pass through the same aperture 13 as the insertion rod. As more fully explained herein, the tip of the extraction tool passes through this keyway, toward an interior position, where the extraction tool can then be locked into position.

Figure 2:
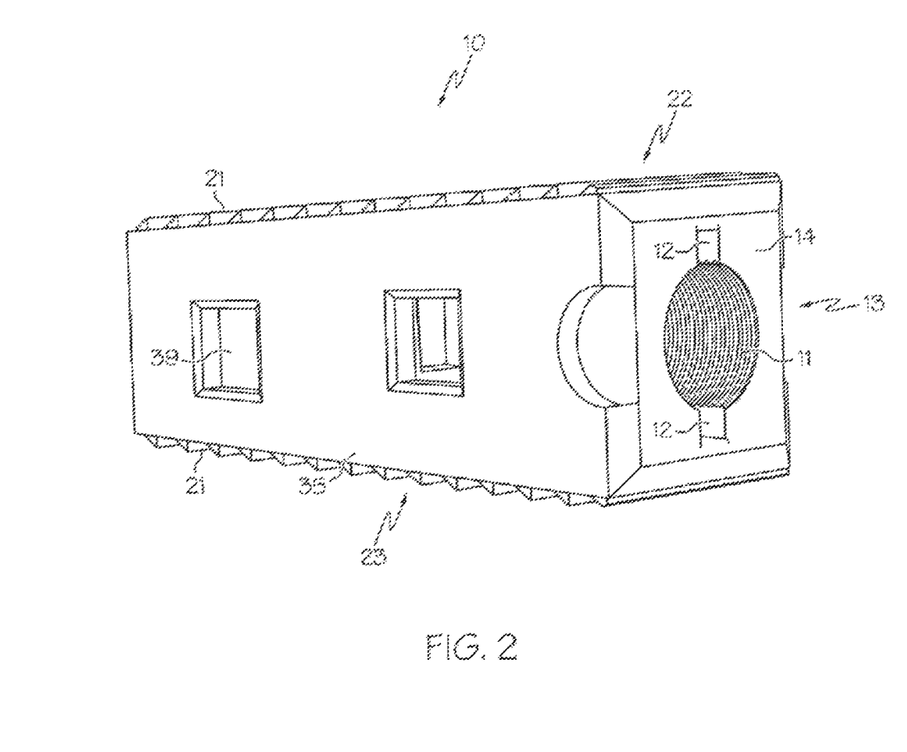
FIG. 2 is an additional perspective view of an interbody spacer device having a face with a keyway passage, according to an embodiment of the present invention.

FIG. 2 displays a lateral view of the spacer 10 showing anti-migration furrows 21 on the superior 22 and inferior 23 surfaces. This is one non-limiting embodiment of the positioning of anti-migration furrows 21. As is known in the art, anti-migration furrows may be advantageously used in order to secure spacer 10 in a desired location and to minimize the risk of movement of the spacer.

Figure 3:
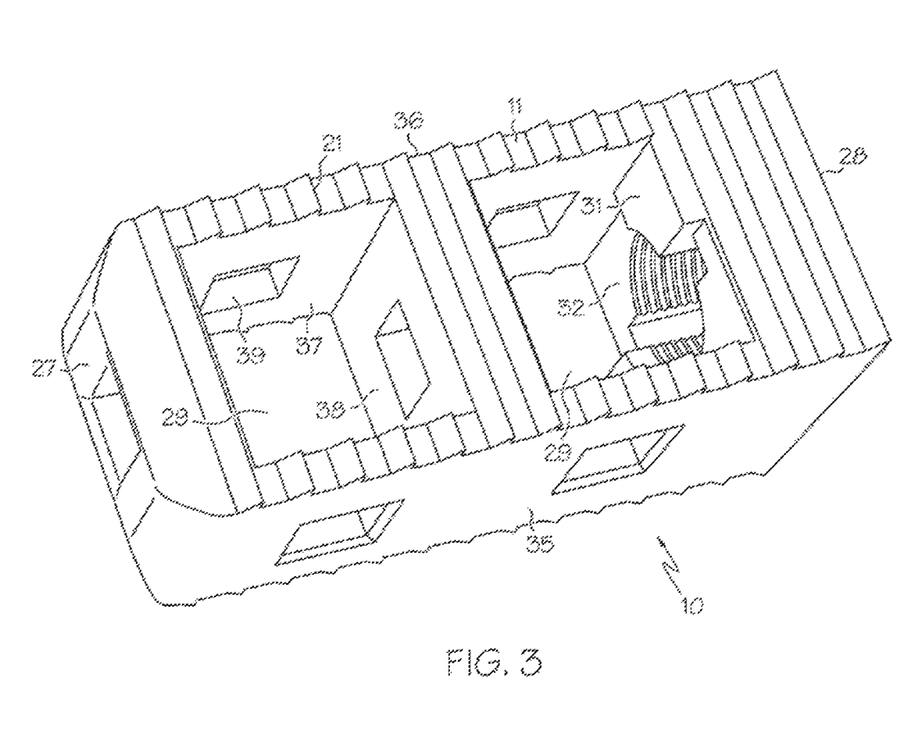
FIG. 3 is a further perspective view of an interbody spacer device showing stop blocks in an inner face, according to an embodiment of the present invention.

FIG. 3 displays a further view of the spacer 10, according to a preferred embodiment. This figure shows stop blocks 31 positioned on an inner face 32 of the spacer. The stop blocks 31 can be used in conjunction with the extraction tool (not shown). As previously explained, the tip of the extraction tool can pass through the aperture 13 of spacer 10 to an interior position. The tip of the extraction tool can then be rotated until tabs on the tip come into contact with the stop block 31 of FIG. 3. The stop block thus limits the rotation of the extraction tool to approximately 90 degrees, for example. Once the retrieval or extraction tool has been rotated to this extent, the surgeon knows that the tool is properly positioned to effect an extraction of the spacer.

Referring generally to FIGS. 1, 2, and 3, it is further noted that the preferred embodiment of spacer 10 can include walls such as a first wall 35 and second wall 36. Walls 35 and 36 may define interior surfaces 37. Further, spacer 10 may include a lateral support 38 which can connect a preferred embodiment of a first wall 35 and a second wall 36. As will be appreciated by those skilled in the art, the overall structure of spacer 10 can vary; however, the preferred embodiment can assist in placement of the spacer in a human patient. Windows 39, optionally configured in walls 35 and 36 can also assist in various surgical procedures such as placement, visual location, and positioning, while also providing areas for tissue connection to the spacer 10. Any cavity 29, constituting an internal space defined by walls 35 and 36 and a top face 28 or 14 and bottom face 27 and lateral support 38 would be of a size so as not to interfere with the interaction between spacer 10 and a tool as described further herein.

Figure 4:
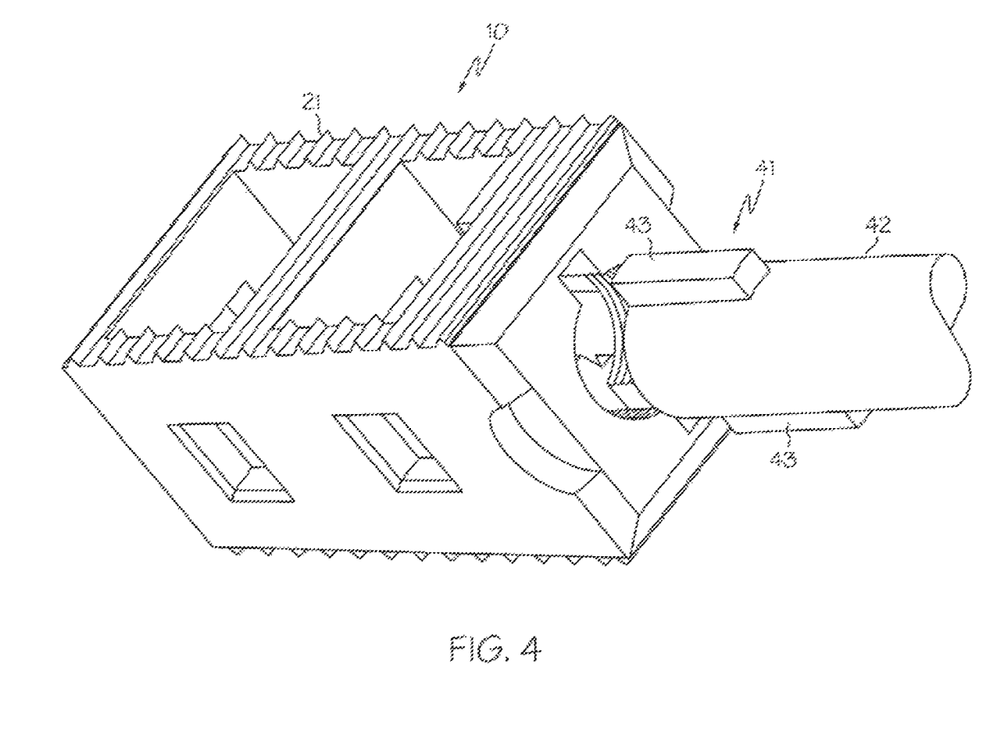
FIG. 4 is a perspective view of a keyed extraction tool aligning with the keyway passage of an interbody spacer, according to an embodiment of the present invention.

Referring now to FIG. 4, there is illustrated an exemplary shape of the tip 41 of an extraction tool 42. In FIG. 4, the tip 41 of the extraction tool 42 has been positioned proximate the face 14 of the spacer 10 such that tabs 43 on the extraction tool 42 are aligned with the key way passages 12 on the face 14. The tool 42 is thus in the proper position to be inserted past the key way 12 to the interior of the spacer 10.

Figure 5:
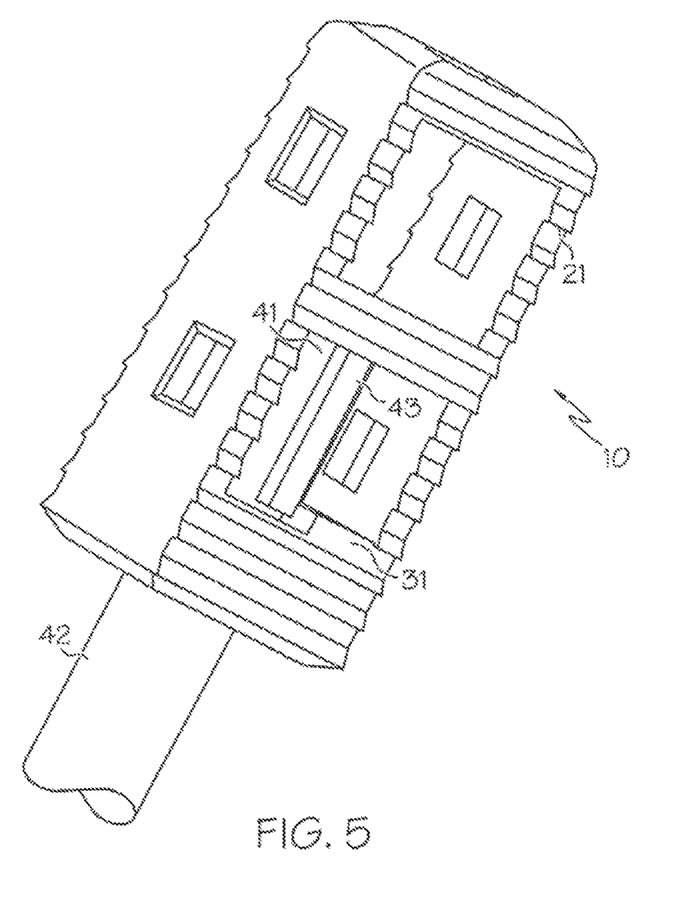
FIG. 5 is a perspective view of an extraction tool engaged with an interbody spacer, according to an embodiment of the present invention.

FIG. 5 illustrates the extraction tool 42 with its tip 41 fully inserted to the interior position of the spacer 10. The tip 41 of the extraction tool 42 is in a position that it can now be rotated to the 90 degree stops 31. It is noted that the extraction tool 42 must be sufficiently inserted such that the tabs 43 positioned on the extraction tool 42 tip 41 have cleared the interface structure of the spacer 10, thus leaving the tabs 43 free to be rotated.

Figure 6:
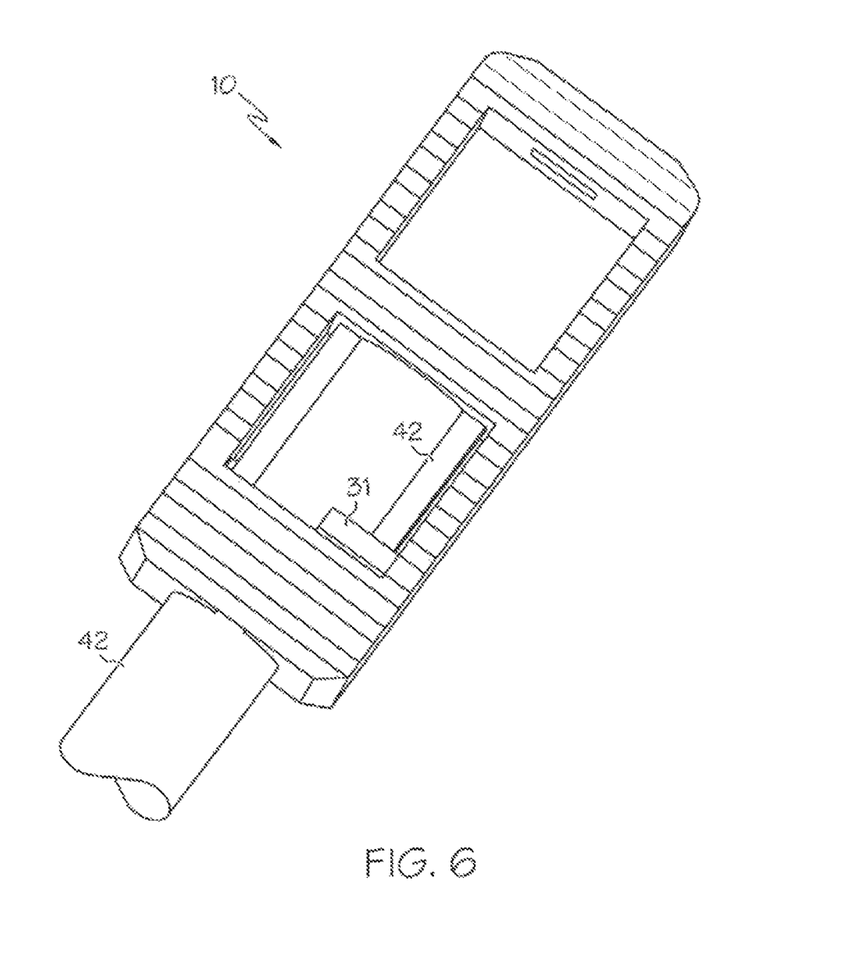
FIG. 6 is a perspective view of an extraction tool engaged and rotated to the locked position with an interbody spacer, according to an embodiment of the present invention.

Referring next to FIG. 6, the extraction tool 42 has been fully rotated to its locked position. In a preferred embodiment, this degree of rotation is approximately 90 degrees, though other degrees of rotation can be chosen. Further, the tool 42 cannot now be extracted without turning back to the original orientation.

It is further noted that in a preferred embodiment the tabs 43 of the extraction tool 42 tip 41 and the interior surface of the spacer face are constructed so as to mutually cooperate so as to facilitate extraction. In the embodiment illustrated, the surface of the tabs 43 that contacts the interior surface 32 of the spacer 10 is substantially flat or planar. Likewise, the interior surface 32 of the spacer 10 is substantially flat or planar. In this manner, when the extraction tool 42 has been inserted into the spacer 10, and rotated to the fullest possible extent, the extraction tool 42 can then be pulled or manipulated so that the tabs 43 make contact with the interior surface 32. At that point of contact force is transferred from the extraction tool 42 to the interbody spacer 10. The mutually flat surfaces thus allow for a good mechanical transfer of force.

Figure 7:
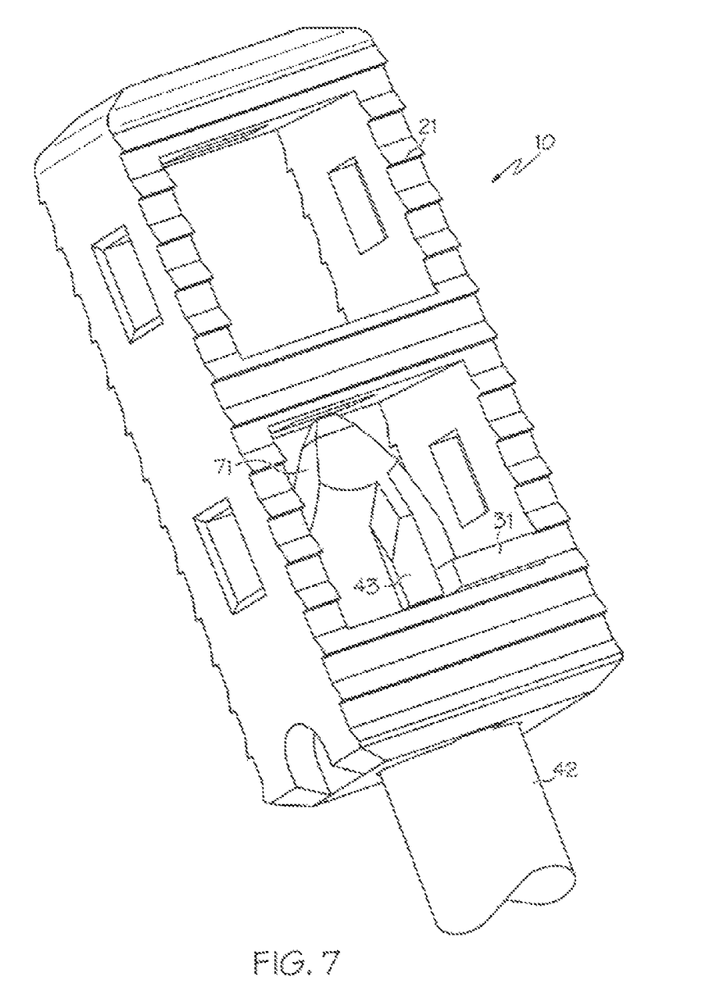
FIG. 7 is a close up perspective view of an extraction tool with a sharpened tip engaged with an interbody spacer, according to an embodiment of the present invention.
Figure 9:
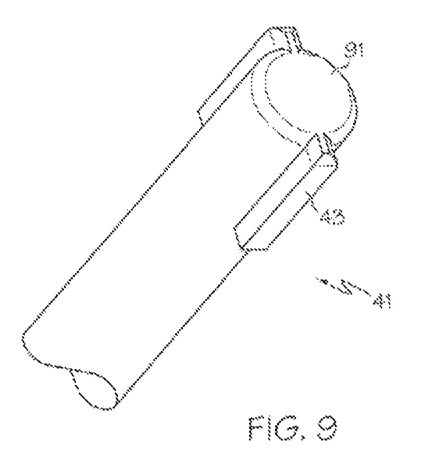
FIG. 9 is a close up perspective view of a blunt tip of an extraction tool, according to an embodiment of the present invention.
Figure 10:
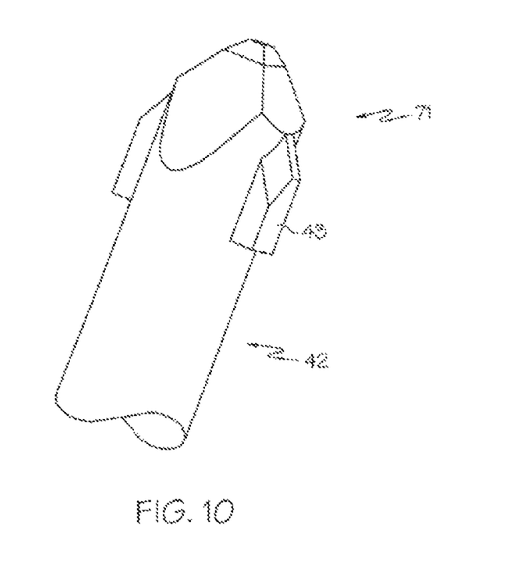
FIG. 10 is a close up perspective view of a sharp tip of an extraction tool, according to an embodiment of the present invention.

Referring now to FIG. 7, there is illustrated an alternative embodiment of an extraction tool tip 41. A sharper version of the extraction tool tip 41, as illustrated, can be used when tissue ingrowth limits the ability of a blunt tipped extractor 42 to be inserted. The sharp tip 71 can more easily cut, crush, and dislodge material within the hollow structure in order to reach its desired fully inserted position. Further this step of cutting through and dislodging tissue ingrowth can assist in providing adequate room within the spacer chamber so as to permit the tool 42 to rotate into the locked position. FIG. 9 provides a close up illustration of a blunt ended tool tip 91, which is also one embodiment of the device. FIG. 10 provides a close up illustration of a sharp tool tip 71, a further embodiment which may be preferred for use in those situations when it is not possible to insert a blunt tipped device due to tissue ingrowth.

Figure 11:
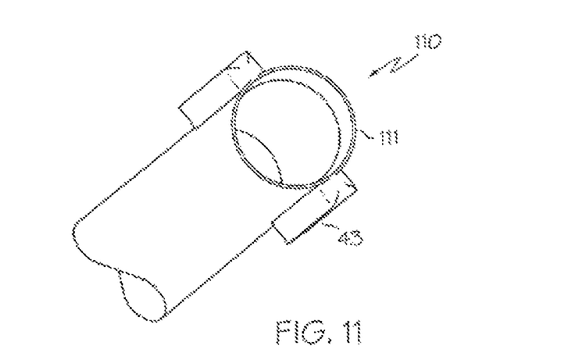
FIG. 11 is a close up perspective view of a hollow tip of an extraction tool, according to an embodiment of the present invention.

Referring now to FIG. 11, there is illustrated an additional embodiment of an extraction tool tip. This embodiment, having a partially or substantially hollow tip 110 presents an alternative design of a tip for use with those situations having tissue ingrowth. The hollowed tip 110 will displace and disturb less material than other embodiments when inserted into the spacer 10. However, the sharpened edges 111 of the hollow tip 110 will cut through scar tissue and trabecular bone. Thus, the tip 110 can be fully inserted so as to allow tip rotation.

At this point, a summary of the use of spacer 10 and extraction tool 42 will here be described. Once spacer 10 has been initially positioned, it may become necessary to remove and/or adjust the positioning of spacer 10. This can be conveniently achieved by assembling the extraction tool 42 with the spacer 10. As previously the tip of the extraction tool 42 is fed through the aperture. The tip must be aligned such that the tabs 43 can pass through the key ways. The tip is sufficiently passed through the aperture until the tabs 43 attached to the tip have passed into the void defined by the spacer 10. In moving the extraction tool, such as passing it through the aperture, a handle or other type of grabbing device may be used on the opposite end of the extraction tool in order to manually manipulate the tool. At this level of clearance, the extraction tool can be rotated such that the tabs 43 on the extraction tool tip have rotated out of alignment with the keyways. A physical confirmation that this has occurred is done by rotating the tool until the tabs 43 come into contact with the blocks 31 positioned on the spacer. At this point the surgeon, or individual handling the extraction tool, can pull on the extraction tool. This manual force is transferred to the spacer where the tabs 43 make contact with the interior surface of the spacer.

Figure 8:
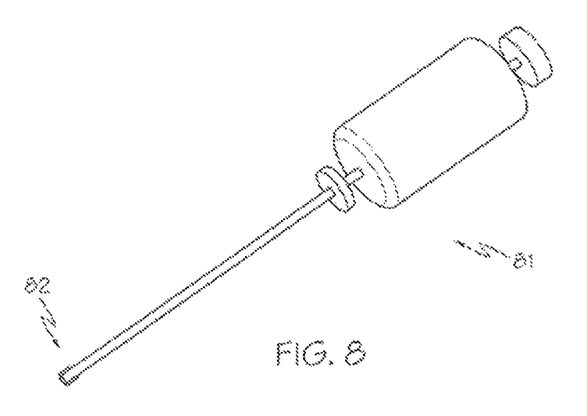
FIG. 8 is a perspective view of a slap hammer and extraction tool assembly, according to an embodiment of the present invention.

Referring now to FIG. 8, there is illustrated a slap hammer assembly 81 with a keyed end 82. The slap hammer 81 can be disassembled and reassembled in the OR (operating room) by unscrewing the end cap to allow the surgeon to place the key into the block without the mass of the slap assembly limiting dexterity and making insertion of the key difficult. The slap hammer 81 takes advantage of the interoperability designed into the existing system between spacer 10 and extraction tool 42. The keyed end 82 of hammer 81 can be designed to engage spacer 10 by passing through the aperture, and rotating until keys make contact with blocks, in a manner similar to that described with respect to extraction tool 42. The keyed end 82 can then be assembled with a hammer portion, if needed. The hammer can then operate under known principles, such as for example momentum hammering as is known in the art. The use of slap hammer 81 would be recommended in those situations where a manual manipulation of an extraction tool would not be sufficient.

Figure 12:
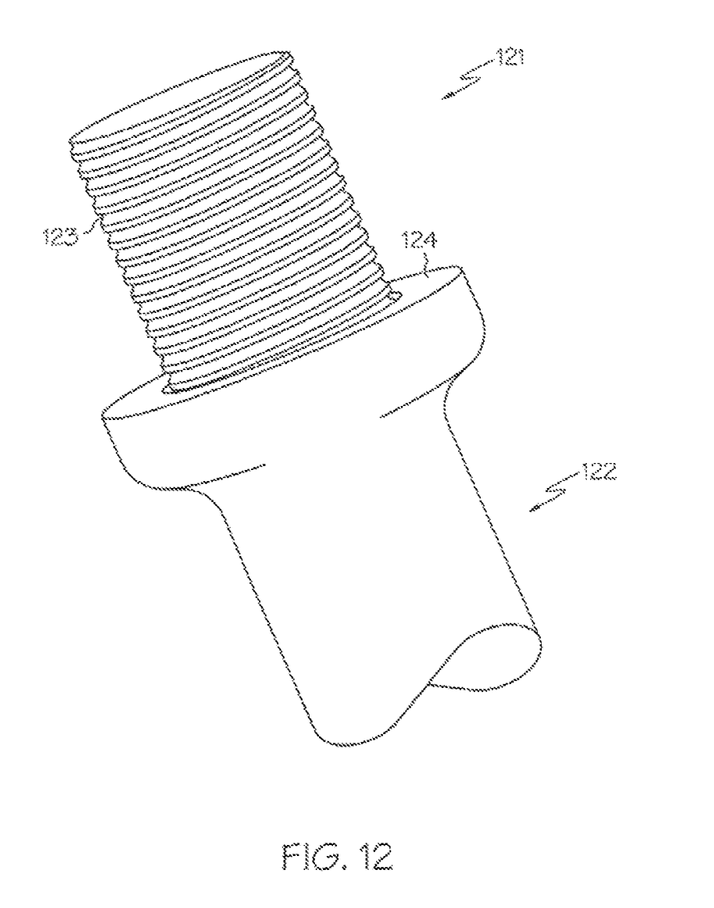
FIG. 12 is a close up perspective view of a tip of an insertion tool, according to an embodiment of the present invention.

Referring next to FIG. 12, there is illustrated a preferred embodiment of the tip portion 121 of an insertion or placement tool 122. The end portion of the rod 122 includes a threaded rod portion 123. This threading 123 is reciprocal threading to that threading 11 on the spacer device 10 (as shown in FIG. 1) and thus allows the placement tool 122 to engage with the interbody spacer 10. When so engaged with the spacer, movement or manipulation of the placement tool 122 can be used to place the interbody device in a desired position.

FIG. 12 also illustrates that the placement tool 122 preferably includes a flared contact face 124. This contact face 124 is brought into contact with a reciprocal face 14 on the interbody spacer 10 when the tool 122 is fully engaged with the spacer 10. In this manner force from the placement tool 122 that is transferred to the interbody spacer 10 is applied not only to the threading 123 but also along the contact face 124. This distributed contact allows the placement tool 122 to ease stress on the threads 123 and distribute force across the face of the implant 10. Also note, in a further preferred embodiment, the chamfered shape to ease withdrawal of the rod and prevent snagging on sensitive tissues.

Figure 13:
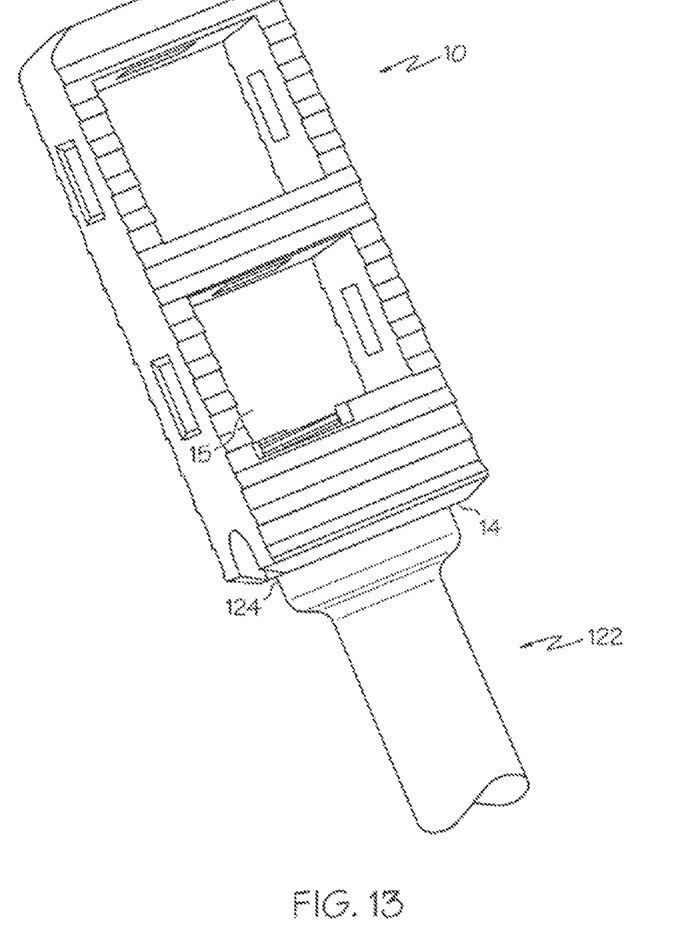
FIG. 13 is a perspective view of an insertion tool engaged with an interbody spacer, according to an embodiment of the present invention.

FIG. 13 shows the insertion rod 122 fully screwed into the interbody device 10. Preferably, the rod tip 121 does not insert far enough to disturb bone graft materials packed into the void 15. As shown, the assembly brings the contact face 124 of the placement tool 122 into contact with the spacer face 14, and thus serves to distribute those forces that might otherwise compromise the plastic screw threads.

Figure 14:
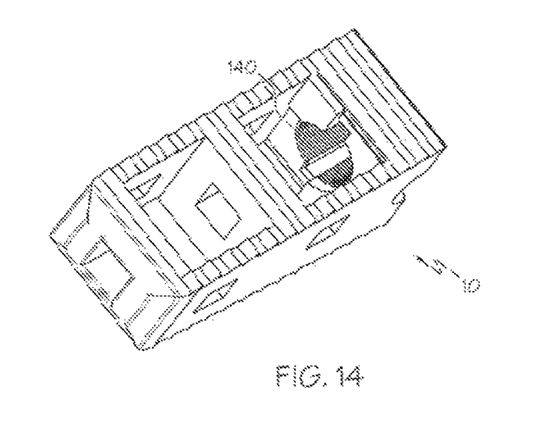
FIG. 14 is a perspective view of an interbody spacer with a backing plate behind one face, according to an embodiment of the present invention.
Figure 15:
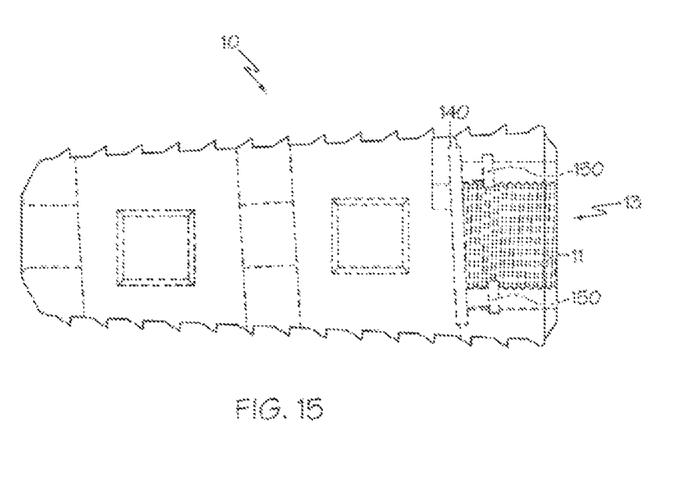
FIG. 15 is a perspective view of an interbody spacer having securing projections connected to the backing plate, according to an embodiment of the present invention.

Referring now to FIGS. 14 and 15, there is illustrated a further embodiment of an interbody spacer 10. In this embodiment, the spacer 10 includes a backing plate 140. Preferably the backing plate 140 is positioned on an interior surface 32 of the spacer 10 as best shown in FIG. 14. Preferably the backing plate 140 is made of a metal or hardened material. An advantage of the backing plate 140 is realized when an extraction tool 42 is fully positioned so as to remove or extract a spacer 10. In such an assembly, the tabs 43 of the extraction tool 42 will now come into contact with the backing plate 140. The hardened nature of the backing plate 140 provides a sturdy platform for receiving force from the extraction tool 42. Preferably, the surface 141 of the backing plate substantially matches the surface 32 of the spacer interior surface 32 on which it rests. Thus, the backing plate 140 can distribute force over a wide area. Also advantageously, the backing plate 140 further reduces the possibility that the interbody spacer 10 may crack or break apart during extraction.

In a preferred embodiment, the backing plate is connected to projections 150, as best shown in FIG. 15. The projections 150 aid in the attachment of the backing plate 140 to the spacer 10. For example, projections 150, which pass from the backing plate 140 into the matrix of the interbody device 10, allow the plate 140 to be secured in place at the time of molding by, in one method, interdigitating with the plastic while it is still malleable. Thus projections 150 allow for a sturdy and robust connection between the plate 140 and the body of the spacer 10.

Figure 16:
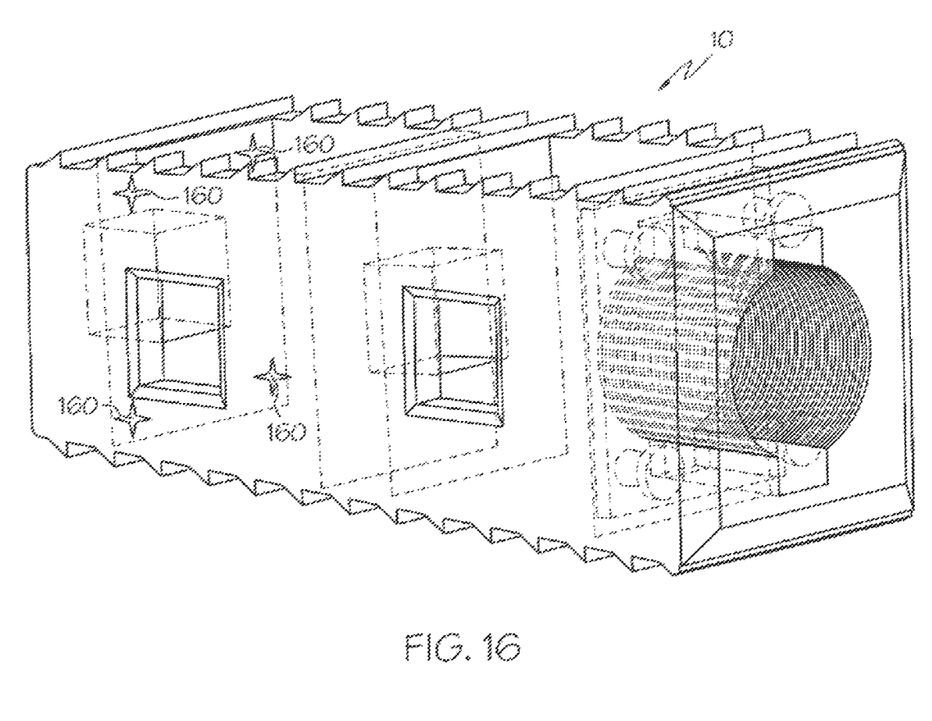
FIG. 16 is a further perspective view of an interbody spacer having radio opaque markers, according to an embodiment of the present invention.

Referring now to FIG. 16 there is shown a further embodiment of an interbody spacer 10. In this figure, radio opaque markers 160 are indicated by stars. Such structures can be placed on or connected to the interbody spacer 10 to assist in placement of the spacer 10. The markers 160 are preferably fabricated of a material that will be identified by a detecting or monitoring instrument, such as for example, radiography or ultrasound. The position of the markers 160, and therefore the position of the spacer 10, can thus be detected in order to assist with placement. The placement of the markers in FIG. 16 is exemplary only.

The device described herein allows a retrieval tool to be locked into the spacer block to ease removal or repositioning of the innerbody spacer. It can be configured in dimensions appropriate for transforaminal lumbar interbody fusion (TLIF), posterior lumbar interbody fusion (PLIF), and anterior lumbar interbody fusion (ALIF) procedures and is not limited to any one technique. The block is inserted using a newly developed threaded rod assembly using an insertion technique that is similar to techniques currently described by other manufacturers of TLIF devices. The device would preferably be manufactured from a material such as a PEEK or similar material. The block could be offered with multiple angle and height options to restore the proper lordosis and spacing at the level of fusion. The block contains voids with interconnections to allow bone graft or bone substitute to be packed inside and to promote tissue ingrowth within the spacer.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out this invention, but that the invention will include all embodiments falling within the scope of the general description.

What is claimed is:

1. A method for manipulating a spinal body spacer for use in spinal surgery on a patient, the method comprising the steps of:

attaching a placement tool to the spinal body spacer by screwing a threaded tip of the placement tool into engagement with a threaded receiving aperture of the spinal body spacer, the spinal body spacer having an outer face and an opposed inner face, the threaded receiving aperture of the spinal body spacer extending completely from the outer face to the inner face, the spinal body spacer comprising keyways connected to the threaded receiving aperture and extending completely from the outer face to the inner face, wherein the spinal body spacer further defines an interior space at least partially defined by the inner face;

manipulating the placement tool so as to locate the spinal body spacer in a desired location;

removing the placement tool by unscrewing the placement tool from the threaded receiving aperture of the spinal body spacer;

passing a tip of an extraction tool through the threaded receiving aperture of the spinal body spacer, the tip of the extraction tool having at least one tab; and rotating the tip of the extraction tool such that the at least one tab of the tip of the extraction tool passes through the keyways of the spacer and extends into the interior space of the spinal body spacer.

2. The method according to claim 1, further comprising the step of receiving positioning information from the spinal body spacer through radio opaque markers located in the interior space of the spinal body spacer.

3. The method according to claim 1 wherein the step of attaching the placement tool further comprises contacting a contact face defined by the positioning tool with a reciprocal face defined by the spinal body spacer to transfer force from the placement tool to the spinal body spacer.

4. The method according to claim 1, wherein the step of rotating the tip of the extraction tool comprises rotating the tip of the extraction tool until the at least one tab of the extraction tool contacts at least one block disposed on an interior surface of the spinal body spacer, the at least one block being configured to restrict rotation of the extraction tool relative to the spinal body spacer;

wherein the method further comprises pulling on the extraction tool to exert a force on the spinal body spacer.

5. The method according to claim 4, further comprising the step of attaching a slap hammer to the extraction tool, wherein the step of pulling on the extraction tool to exert a force on the spinal body spacer comprises applying a force to the slap hammer to pull on the extraction tool.

6. The method according to claim 1, wherein the spinal body spacer further comprises:

a superior surface;
an inferior surface; and
a plurality of antimigration furrows positioned on each of the superior surface and the inferior surface.

7. The method according to claim 1, wherein the tip of the extraction tool is substantially blunt.

8. The method according to claim 1, wherein the tip of the extraction tool is substantially pointed.

9. The method according to claim 1, wherein the tip of the extraction tool comprises a hollow area.

10. The method according to claim 9, wherein the tip of the extraction tool comprises a sharp edge disposed substantially around the hollow area.

11. The method according to claim 1, wherein the spinal body spacer further comprises a backing plate positioned on the inner face of the spinal body spacer, wherein the backing plate is configured to receive force from the extraction tool and to reinforce the inner face of the spinal body spacer.

12. The method according to claim 11, wherein the backing plate further comprises projections disposed in a matrix of the spinal body spacer.

13. The method according to claim 1, wherein the spinal body spacer further comprises a first wall and a second wall connected by a first face, a second face, and a lateral support, wherein the first face of the spinal body spacer comprises the outer face of the spinal body spacer.

14. The method according to claim 13, wherein the first wall and the second wall define a plurality of windows.

15. A method for manipulating a spinal body spacer for use in a medical procedure, the method comprising the steps of:
    positioning the spinal body spacer in a first desired location, the spinal body spacer comprising:
       a first wall;
       a second wall, the first and second walls being connected by a first face, a second face, and a lateral support;
       an interior space at least partially defined by the second face;
       a threaded aperture extending completely from the first face to the second face; and
       at least one keyway connected to the threaded aperture and extending completely from the first face to the second face; and
    moving the spinal body spacer from the first desired location by passing a tip of an extraction tool through the threaded aperture of the spinal body spacer and passing at least one tab of the tip of the extraction tool through a keyway of the spinal body spacer, wherein, upon full engagement between the extraction tool and the spinal body spacer, the at least one tab of the tip of the extraction tool extends into the interior space of the spinal body spacer.

16. The method according to claim 15, further comprising applying a force to the extraction tool to adjust the position of the spinal body spacer to a second desired location, wherein the second desired location is different from the first desired location.

17. The method according to claim 16, further comp sing positioning a slap hammer assembly in engagement with the extraction tool, wherein the step of applying a force to the extraction tool comprises applying a force to the slap hammer assembly to apply the force to the extraction tool.

* * * * *